US009417179B2

(12) United States Patent
Wada (10) Patent No.: US 9,417,179 B2
(45) Date of Patent: Aug. 16, 2016

(54) ACOUSTIC WAVE ACQUISITION APPARATUS (75) Inventor: Yoshiko Wada, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 203 days.

(21) Appl. No.: 13/984,415

(22) PCT Filed: Feb. 6, 2012

(86) PCT No.: PCT/JP2012/000776
§ 371 (c)(1),
(2), (4) Date: Dec. 4, 2013

(87) PCT Pub. No.: WO2012/108170
PCT Pub. Date: Aug. 16, 2012

(65) Prior Publication Data
US 2014/0086016 A1 Mar. 27, 2014

(30) Foreign Application Priority Data

Feb. 10, 2011 (JP) ................................. 2011-027320

(51) Int. Cl.
*G01V 1/18* (2006.01)
*G01N 21/17* (2006.01)
*A61B 5/00* (2006.01)

(52) U.S. Cl.
CPC .......... *G01N 21/1702* (2013.01); *A61B 5/0095* (2013.01)

(58) Field of Classification Search
CPC ........................... G01N 21/1702; A61B 5/0095
USPC ......................................................... 367/178
See application file for complete search history.

(56) References Cited

U.S. PATENT DOCUMENTS

| 5,713,356 | A | 2/1998 | Kruger | |
|---|---|---|---|---|
| 2004/0220479 | A1 | 11/2004 | Wake et al. | |
| 2007/0299341 | A1 | 12/2007 | Wang et al. | |
| 2008/0173093 | A1 | 7/2008 | Wang et al. | |
| 2009/0079987 | A1* | 3/2009 | Ben-Ezra et al. | 356/445 |
| 2010/0179434 | A1 | 7/2010 | Thornton | |
| 2011/0306865 | A1* | 12/2011 | Thornton et al. | 600/407 |

FOREIGN PATENT DOCUMENTS

| CN | 201207035 Y | 3/2009 |
|---|---|---|
| CN | 101827556 A | 9/2010 |
| CN | 101990417 A | 3/2011 |
| CN | 102137618 A | 7/2011 |
| EP | 2003472 A1 | 12/2008 |
| EP | 2148183 A1 | 1/2010 |
| JP | 2002-536041 A | 10/2002 |
| JP | 2010-012295 A | 1/2010 |
| WO | 98/23206 A1 | 6/1998 |
| WO | 2008/146225 A1 | 12/2008 |
| WO | 2010/030817 A1 | 3/2010 |

* cited by examiner

*Primary Examiner* — Mark Hellner
(74) *Attorney, Agent, or Firm* — Canon U.S.A. Inc., IP Division (57) ABSTRACT

In a conventional device, light is irradiated from positions on a rotation axis of a detector, so that there may be unevenness of light irradiation intensity in a subject.

The acoustic wave acquisition apparatus of the present invention includes a light source that generates light and a detector including a plurality of elements that receive an acoustic wave generated from inside a subject when the subject is irradiated with the light. The acoustic wave acquisition apparatus further includes a rotation driving unit that rotates the detector and a plurality of light irradiation portions that irradiate the subject with the light from the light source. The plurality of light irradiation portions are provided at least at positions other than a rotation axis of the detector.

27 Claims, 10 Drawing Sheets

ACOUSTIC WAVE ACQUISITION APPARATUS

TECHNICAL FIELD

The present invention relates to an acoustic wave acquisition apparatus.

BACKGROUND ART

A photoacoustic imaging method is proposed as a technique for imaging the inside of a subject using acoustic waves (typically, ultrasonic waves). The photoacoustic imaging method is a method for visualizing information related to optical characteristic values inside a subject by using acoustic waves generated by irradiating the subject with pulse laser light.

Figure 10:
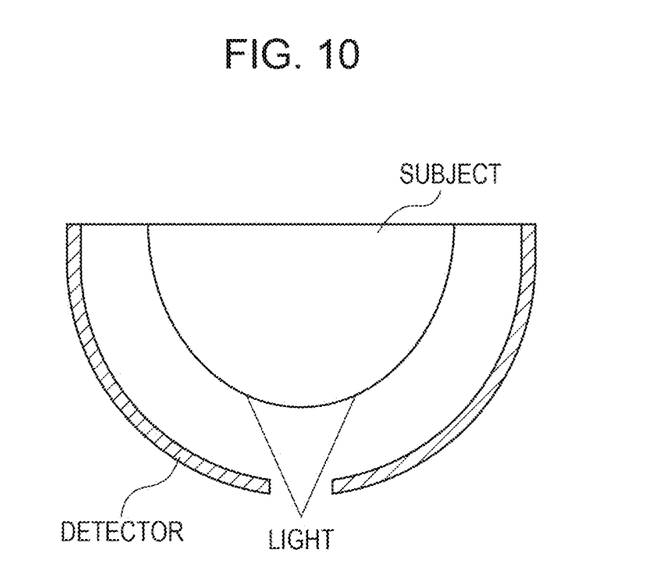
FIG. 10 is a schematic diagram for explaining a light irradiation method of a conventional example.

PTL 1 describes a method for receiving acoustic waves from a subject (a breast) by using a plurality of transducers arranged on a hemisphere surface and generating (reconstructing) three-dimensional image data. FIG. 10 is a schematic diagram showing an appearance of a detector described in PTL 1. FIG. 10 shows a state in which the subject is irradiated with light. On this device, a subject person inserts her breast into the hemispherical detector to which transducers are arranged and the subject person lies on her stomach. A gap between the inserted breast and the transducers is filled with water to perform acoustic matching. When measurement is performed, the detector to which the transducers are arranged rotates step by step and the transducers receive acoustic waves at each position. The rotation axis is an axis passing through the top of the hemisphere and the center of the hemisphere. The detector rotates in this way, so that it is possible to perform measurement as if transducers were present in many directions even when a small number of transducers are used. The breast is inserted to be located near the center of the hemisphere of the detector, and pulse light is irradiated from the top portion of the hemisphere on a rotation axis of the detector.

CITATION LIST

Patent Literature

PTL 1: U.S. Pat. No. 5,713,356

SUMMARY OF INVENTION

The acoustic wave generated from the subject is proportional to the light intensity at the position at which the acoustic wave is generated. Therefore, when generating image data by using the photoacoustic imaging method, it is desirable to irradiate the subject with light having a uniform intensity. If the intensity of the irradiated light is uneven, the intensity of the generated acoustic waves becomes uneven, so that the contrast distribution of reconstructed image is generated without respect to the contrast distribution of an object (light-absorbing body) in the subject.

When measurement is performed by using the device shown in FIG. 10, the subject person lies on her stomach and inserts her breast into the inside of the detector having an opening in the upper portion thereof. The pulse light is irradiated from the rotation axis direction, so that an intense light is irradiated near the nipple, and the intensity of the light irradiated near the chest wall weakens due to attenuation. Therefore, the acoustic waves from the nipple portion are strong and the contrast of the image is high. On the other hand, the acoustic waves from the chest wall portion are weak and the contrast of the image is low. As described above, in the device of PTL 1, the light is irradiated only from the rotation axis direction, so that the light irradiation position does not change. Therefore, unevenness of light irradiation intensity occurs in the subject.

In view of the above problem, the present invention provides an acoustic wave acquisition apparatus that reduces the unevenness of light irradiation intensity in a rotation-type detector.

The acoustic wave acquisition apparatus of the present invention includes a light source that generates light and a detector including a plurality of elements that receive an acoustic wave generated from inside a subject when the subject is irradiated with the light. The acoustic wave acquisition apparatus further includes a rotation driving unit that rotates the detector and a plurality of light irradiation portions that irradiate the subject with the light from the light source. The plurality of light irradiation portions are provided at least at positions other than a rotation axis of the detector.

According to the present invention, it is possible to reduce unevenness of the intensity of the light hit on the subject by irradiating the subject with light from at least a direction other than the rotation axis direction.

DESCRIPTION OF EMBODIMENTS

Hereinafter, the present invention will be described with reference to the drawings.

Figure 1A:
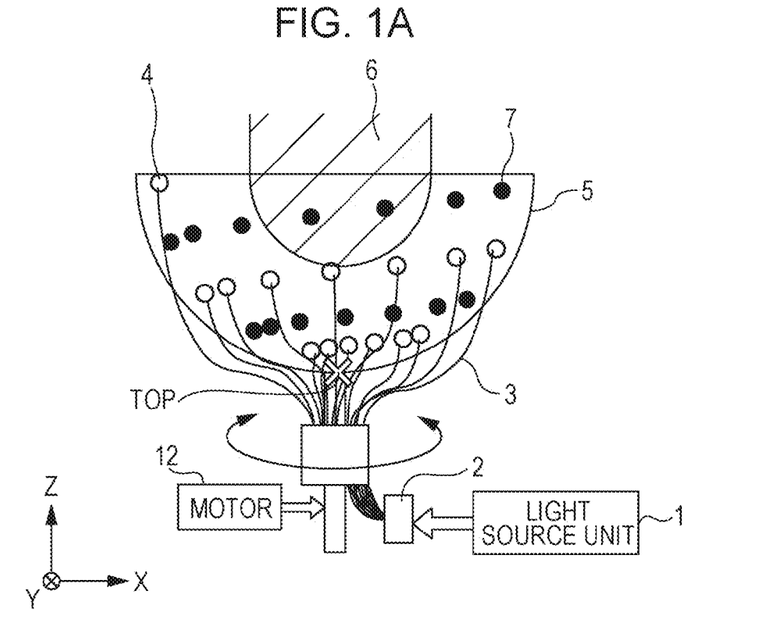
FIG. 1A is a schematic diagram for explaining an acoustic wave acquisition apparatus according to a first embodiment of the present invention.
Figure 1B:
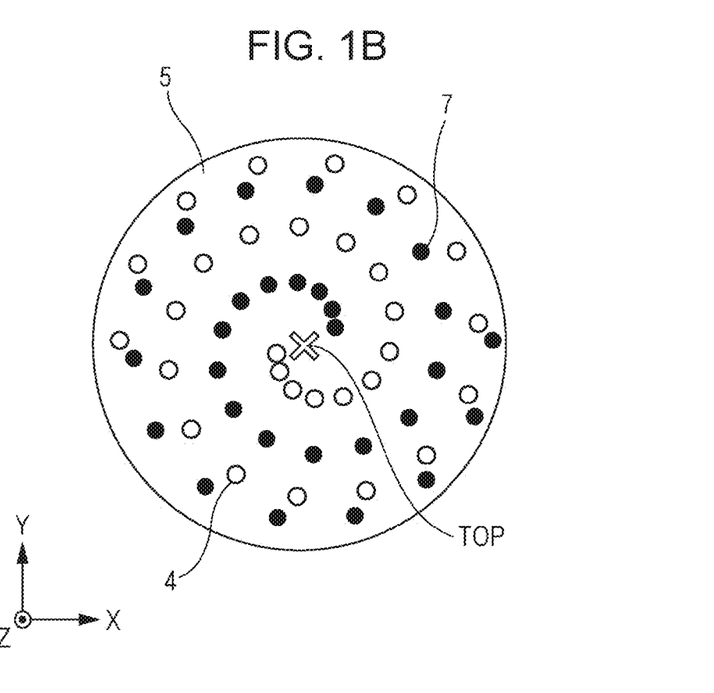
FIG. 1B is a schematic diagram for explaining the acoustic wave acquisition apparatus according to the first embodiment of the present invention.
Figure 2:
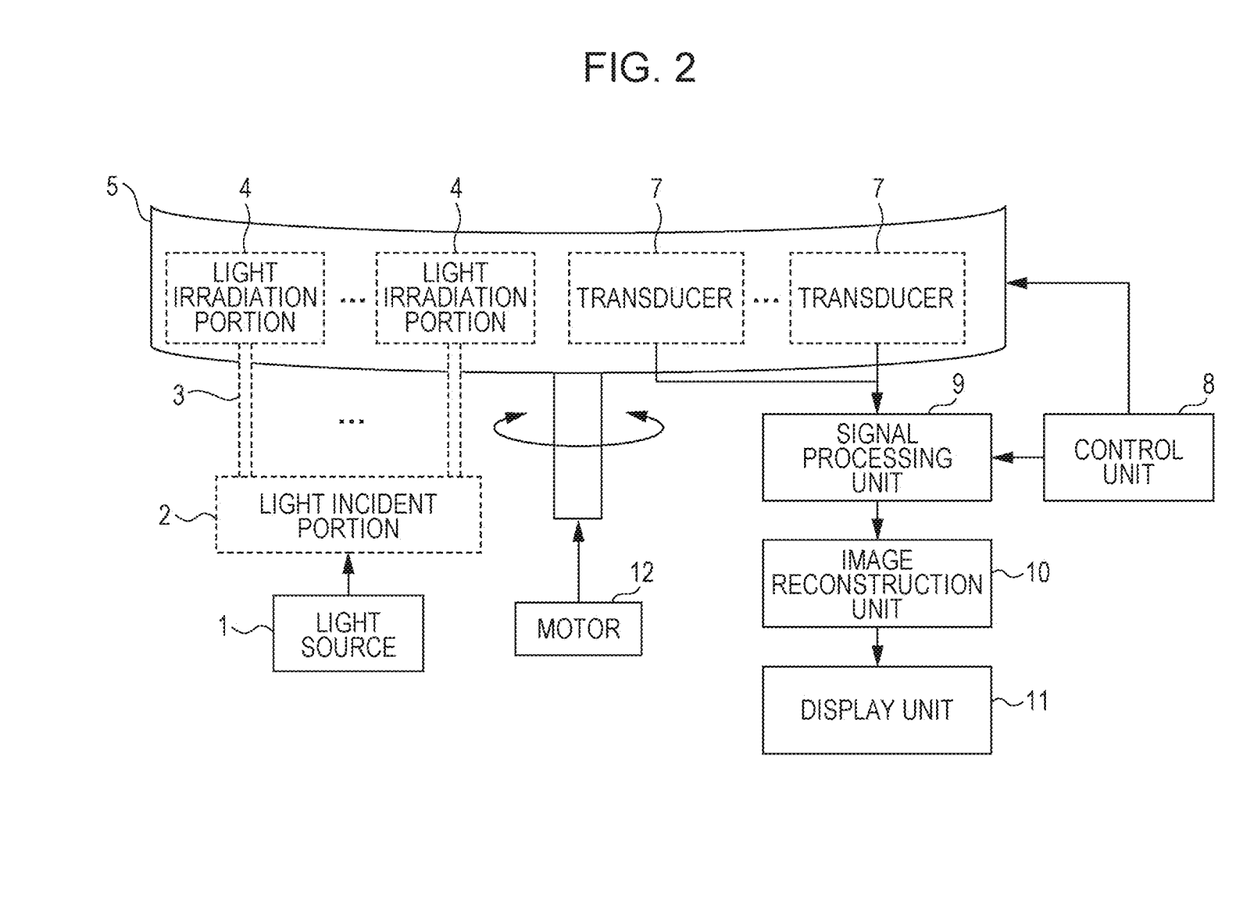
FIG. 2 is a block diagram for explaining the device according to the first embodiment of the present invention.

A basic embodiment of an acoustic wave acquisition apparatus to which the present invention can be applied will be described with reference to FIGS. 1 and 2. FIGS. 1A and 1B are schematic diagrams showing a configuration of the acoustic wave acquisition apparatus to which the present invention can be applied. FIG. 1A is a cross-sectional view showing a structure around a detector 5 and an arrangement of a subject 6. FIG. 1B is a top view showing an arrangement of transducers 7 and light irradiation portions 4. FIG. 2 is a block diagram showing a configuration of the acoustic wave acquisition apparatus to which the present invention can be applied.

The acoustic wave acquisition apparatus of the present invention includes a plurality of transducers 7, a light source 1 that generates pulse light, and a plurality of light irradiation portions 4 that irradiate the subject 6 with the pulse light generated by the light source 1. The plurality of transducers 7 are arranged on the detector 5 having a hemispherical shape so that the transducers 7 surround the subject 6. The detector 5 is rotated around a predetermined rotation axis by a motor 12 which is a rotation driving unit. The light generated by the light source 1 is transmitted to the light irradiation portions 4 by a waveguide unit 3.

The transducer 7 is an element for receiving an acoustic wave and converting the acoustic wave into an electrical signal. The transducers 7 are arranged on the detector 5 as indicated by black circles in FIG. 1B. The positions of the light irradiation portions 4 that irradiate the subject 6 with the pulse light are indicated by white circles in FIG. 1B. When the light irradiation portions 4 irradiate the subject 6 with the light, an object (light-absorbing body) such as hemoglobin absorbs the light and generates an acoustic wave having an intensity corresponding to the intensity of the absorbed light. The generated acoustic wave is received by the transducers 7 fixed to the detector 5 and converted into electrical signals.

The detector 5 rotates to rotationally move the transducers 7 and the light irradiation portions 4. At positions to which the transducers 7 and the light irradiation portions 4 are moved, light is irradiated from the light irradiation portions 4, and the transducers 7 receive the generated acoustic wave and output electrical signals. The movement and light irradiation are repeatedly performed in this way, and the acoustic waves from the subject 6 are measured. The electrical signals outputted from the transducers 7 are digitalized by a signal processing unit 9 and then recorded separately for each receiving position at which the acoustic wave is received. An image reconstruction unit 10 reconstructs image by using the electrical signals of each receiving position and generates image data. The generated image data is inputted into a display unit 11 and displayed as an image.

The device described above includes a plurality of light irradiation portions 4 fixed to positions other than the rotation axis of the detector 5 and the light irradiation portions 4 rotate along with the transducers 7, so that light can be irradiated from a plurality of positions around the subject. Therefore, it is possible to reduce unevenness (variations) of the light irradiation intensity.

Hereinafter, each component will be described in detail.

Light Source

The light source 1 is a unit for irradiating light having a specific wavelength absorbed by a specific component (for example, hemoglobin) included in the subject (for example, living organism). The light source 1 includes at least one pulse light source capable of generating pulse light of 5 to 50 nanoseconds. Although the light source 1 is desired to be a laser having a large output power, a light-emitting diode or the like can be used instead of laser. As the laser, various lasers such as a solid-state laser, a gas laser, a dye laser, a semiconductor laser can be used. In the present invention, the light means an electromagnetic wave including visual light and infrared light. Specifically, light having a wavelength in a range from 500 nm to 1300 nm is used. Light having a specific wavelength in the above range may be used depending on the component to be measured. The timing, wavelength, intensity, and the like of the irradiation are controlled by a light source control unit not shown in the drawings.

Light Irradiation Portion

The light irradiation portion 4 irradiates the light from the light source 1 to the subject 6. In the present invention, the light irradiation portions are provided at positions other than the rotation axis of the detector. The light irradiation portion provided at a position other than the rotation axis of the detector can irradiate light from another position with respect to the subject by the rotation of the detector, so that the light irradiation portion can irradiate light from a plurality of positions. The light irradiation portion may be provided on the rotation axis. Examples of the light irradiation portion 4 include a lens and a diffuser panel. When an optical fiber is used as the waveguide unit 3, the light irradiation portion 4 may be the front end portion of the optical fiber.

When there is a light-absorbing body having a uniform absorbing coefficient in the subject 6, the intensity of the acoustic wave from the light-absorbing body in the subject 6 is desired to be uniform regardless of the positions in the subject 6. When the light irradiation area is large, the light intensity distribution in the subject 6 is smooth, so that the intensity distribution of the acoustic wave is also smooth. Therefore, when the subject is irradiated with light, it is desired that the light is widened and a large area of the subject 6 is irradiated with the light. Therefore, it is desired that a diffuser panel and a plano-concave lens are arranged in the light irradiation portion 4 and the irradiation area is widened.

Waveguide Unit

The waveguide unit 3 transmits light from the light source 1 to the light irradiation portion 4. Examples of the waveguide unit 3 include optical members such as an optical fiber, a diffuser such as an integrating sphere, a mirror that reflects light, a lens that collects, enlarges, or deforms light, and a prism that diffuses/refracts/reflects light. As the waveguide unit 3, one of these optical members may be used or a combination of these optical members may be used. The light incident portion 2 is a portion from which the light from the light source enters the waveguide unit 3. When an optical fiber is used as the waveguide unit 3, the light incident portion 2 may be an end portion (opposite to the light irradiation portion 4) of the optical fiber. As the light incident portion 2, an optical member such as a lens, a mirror, and a prism may be used.

Transducer

The transducer 7 is an element that receives an acoustic wave and converts the acoustic wave into an electrical signal. The transducer 7 is disposed on the detector 5 with a receiving surface facing the subject 6. It is desired that the transducers 7 are arranged so that the transducers 7 receive acoustic waves from a plurality of positions in a wide area when the detector 5 rotates. For example, elements of the transducers 7 are arranged in a helical shape as shown in FIG. 1B, so that the transducers 7 can receive acoustic waves a wide area. As the transducer 7, any element that receives an acoustic wave and converts the acoustic wave into an electrical signal can be used, such as a conversion element like a PZT that uses a piezoelectric phenomenon, a conversion element that uses an optical resonation, and a conversion element like a CMUT that uses capacitance change.

Detector

The detector 5 has a container shape into which the subject is inserted. Transducers 7 are arranged on the detector 5. In FIG. 1A, the transducers 7 and the light irradiation portions 4 are arranged in a helical shape so that the transducers 7 and the light irradiation portions 4 surround the subject 6. The detector 5 is rotated around a predetermined rotation axis by the motor 12 which is a rotation driving unit. In FIG. 1A, the rotation axis is a line passing through the top of the hemisphere and the center of the hemisphere. Although, in FIG. 1, the detector 5 is a container whose inner wall facing the subject has a hemispherical shape, the inner wall may have a semielliptical shape, a rectangular solid shape, or a cylindrical shape. When measurement is performed, in the detector 5, a gap between the transducers 7 and the subject 6 is filled with an acoustic matching material to perform acoustic matching. Examples of the acoustic matching material include water and castor oil.

The detector 5 may rotate step by step, that is, the detector 5 may rotate by a specific angle at a time. Or, the detector 5 may rotate continuously. The control unit 8 performs control related to the rotation such as the rotation angle, the number of rotations, and the movement for returning to an initial position after the measurement. The rotation angle and the number of rotations can be inputted by an operator from an input unit not shown in the drawings. The control unit 8 outputs the rotation angle and the number of rotations of the detector 5 to the signal processing unit 9.

Signal Processing Unit

The signal processing unit 9 amplifies the electrical signals outputted from the transducers 7 and performs A/D conversion. Then, the signal processing unit 9 records the electrical signals in association with positions at which the acoustic waves are received. While the detector 5 rotates during measurement, the signal processing unit 9 records the electrical signals. After the detector 5 stops rotating, the detector 5 outputs the electrical signals to the image reconstruction unit 10.

Image Reconstruction Unit

The image reconstruction unit 10 reconstructs an image on the basis of the signals outputted from the signal processing unit 9 and generates image data. The obtained image data indicates information distribution related to optical characteristic values in the subject 6. Specifically, the image data indicates a generation source distribution of the acoustic waves, an initial acoustic pressure distribution in the subject, a light energy absorption density distribution derived from the initial acoustic pressure distribution, an absorption coefficient distribution, and a density distribution of the material included in the tissues. The density distribution of the material is, for example, a distribution of degrees of oxygen saturation and an oxygenated/reduced hemoglobin density distribution.

As an image reconstruction algorithm for generating the image data, for example, back projection in the time domain or the Fourier domain normally used in tomography technique can be used. If a long time can be used to reconstruct an image, an image reconstruction method such as an inverse problem analysis method (iterative method) by an iteration process can also be used. Typical examples of PAT image reconstruction method include a Fourier transform method, a universal back-projection method, and a filtered back-projection method.

Display Unit

The display unit 11 displays the image data outputted from the image reconstruction unit 10 as an image. The displayed image may be a MIP (Maximum Intensity Projection) image and a slice image. However other display methods can be used. It is possible to display a 3D image from a plurality of directions and change the inclination and the display area of the displayed image, the window level, and the window width while checking the display.

Next, the embodiments of the present invention will be described.

First Embodiment

In the present embodiment, an example in which the acoustic wave acquisition apparatus shown in FIG. 1 is used will be described. In the acoustic wave acquisition apparatus of the present embodiment, the light irradiation portion 4 irradiates the subject 6 with the light from the light source though the wave guide means 3. A plurality of optical fibers having a diameter of 0.1 mm to 1 mm are bundled together and used as the waveguide unit 3. In the present embodiment, a concave lens and a convex lens are used as the light incident portion 2. The light from the light source is widened by the concave lens and formed into a parallel light by the convex lens, and the light is put into the optical fibers which are the waveguide unit 3.

The transducers 7 are arranged in a helical shape starting from the top of the hemisphere of the detector 5 having a hemispherical surface. The diameter of the detector 5 needs to be larger than the subject, so that the diameter may be greater than or equal to 200 mm and smaller than or equal to 350 mm. The light irradiation portions 4 are arranged in a helical shape formed by rotating the helical shape which is formed by the transducers 7 by 180 degrees around the rotation axis. As shown in FIG. 1B, the light irradiation portions 4 are mounted in a helical shape, so that when the light irradiation portions 4 rotate 360 degrees, light can be irradiated from almost all directions to the inserted subject 6. Although, in FIGS. 1A and 1B, 30 transducers 7 are arranged in an array shape and also 30 light irradiation portions 4 are arranged in the same manner, the present invention is not limited to this.

When an image is reconstructed by the photoacoustic imaging method, it is desired that the acoustic waves from the subject 6 are received from a plurality of directions. The detector 5 of the present embodiment rotates 360 degrees step by step in 16 steps around the rotation axis. The detector 5 rotates 360 degrees, so that it is necessary to prevent the transducers 7 and the optical fibers from being entangled. Therefore, as shown in FIG. 1A, a structure in which cords of the transducers 7 and the optical fibers are held together on the rotation axis may be employed.

Figure 9A:
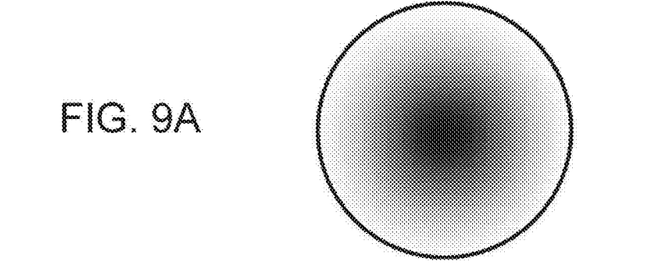
FIG. 9A is a schematic diagram showing the light intensity distribution formed by a conventional example.
Figure 9B:
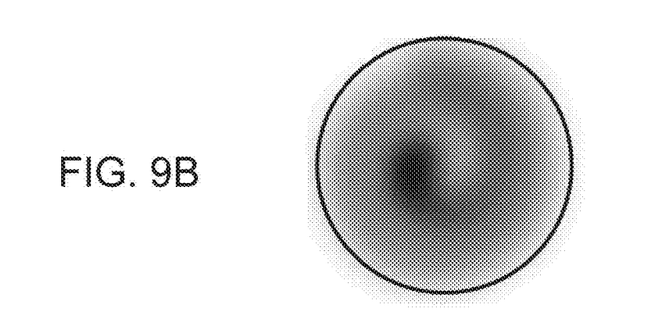
FIG. 9B is a schematic diagram showing the light intensity distribution formed by the first embodiment of the present invention.

As in the present embodiment, the light irradiation portions 4 are widely arranged on the detector 5, so that the light can be irradiated to the side surfaces of the subject 6. FIGS. 9A, 9B, 9C, and 9D are schematic diagrams showing the light intensity distribution as seen from above. FIG. 9B shows the light intensity distribution formed by the present embodiment. FIG. 9A is the light intensity distribution when the light is irradiated only from the rotation axis direction (conventional example). It is found that the light is irradiated to a large area on the detector in FIG. 9B as compared with FIG. 9A, so that a large amount of light is irradiated near the chest wall of the breast (marginal area of the detector, that is, near the opening portion). In the configuration of the present embodiment, a large amount of light is irradiated near the chest wall as compared with a case in which light is irradiated from one direction, so that unevenness of the intensity of light irradiated into the subject 6 is reduced. Further, unevenness of the contrast of the obtained image data is reduced.

Second Embodiment

The acoustic wave acquisition apparatus of the present embodiment is characterized in that a plurality of light irradiation portions 4 are arranged rotationally symmetrically around the rotation axis of the detector 5.

In the first embodiment, when the detector 5 rotates, the light irradiation portions 4 maintain the same positional relationship with the positions of the transducers 7. However, the positional relationship between the light irradiation portions 4 and the subject 6 changes by the rotation. Thereby, the distribution of the light irradiated to the subject 6 changes for each rotation position. In the present embodiment, the light irradiation portions 4 are arranged rotationally symmetrically around the rotation axis so that the light irradiation positions are not changed by the rotation of the detector 5. A unit angle of a rotation step is an integral multiple of the arrangement angle of the light irradiation portions. The present embodiment is the same as the first embodiment except for the arrangement positions of the light irradiation portions 4, so that the differences from the first embodiment will be mainly described below.

Figure 3A:
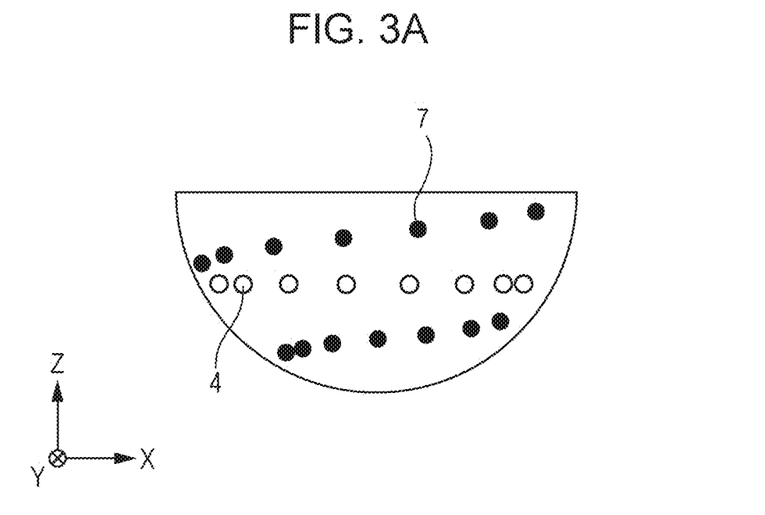
FIG. 3A is a schematic diagram for explaining a transducer and a light irradiation position according to a second embodiment of the present invention.
Figure 3B:
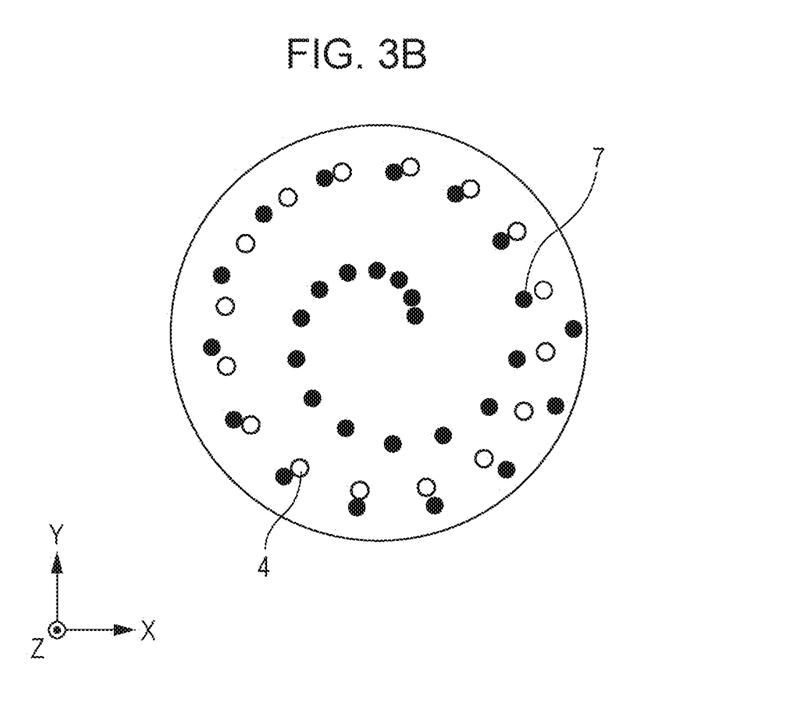
FIG. 3B is a schematic diagram for explaining the transducer and the light irradiation position according to the second embodiment of the present invention.

FIGS. 3A and 3B show the positions of the transducers 7 and the positions of the light irradiation portions 4 on the detector 5. In the present embodiment, the light irradiation positions are arranged rotationally symmetrically around the rotation axis as shown in FIG. 3B. In FIGS. 3A and 3B, 30 transducers are arranged on the detector 5. At the depth of 50 mm from the opening of the detector 5, 16 light irradiation portions are arranged at unit angles of 22.5 degrees around the rotation axis.

It is desired that the light from the light irradiation portions 4 is three-dimensional rotationally symmetric, so that the light is irradiated to a position on the rotation axis. The arrangement of the light irradiation portions 4 has a symmetric property of 16 axes. The number of the rotation steps is set to 16/n (n is an integer), so that the positional relationship between the light irradiation portions 4 and the subject 6 does not change before and after the rotation of the detector 5.

Figure 9C:
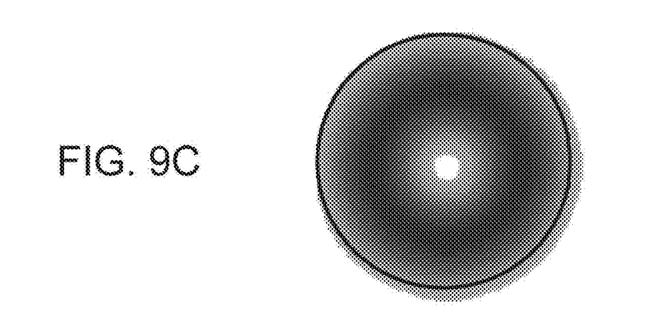
FIG. 9C is a schematic diagram showing the light intensity distribution formed by the second embodiment of the present invention.

FIG. 9C shows the light intensity distribution obtained by the present embodiment. As shown in FIG. 9C, in the present embodiment, even when the detector 6 is rotated, the variation of the light intensity distribution is small, so that unevenness of the light intensity between measurements due to the rotation is reduced.

Although, in the present embodiment, the light irradiation portions 4 are arranged rotationally symmetrically only at one height (at a specific position in the rotation axis direction), the light irradiation portions 4 may be arranged at a plurality of heights (at a plurality of positions in the rotation axis direction). At each height, the light irradiation portions, the number of which is an integral multiple of the steps (the number of the steps*n), are arranged at regular intervals. At this time, the number of axes of symmetry may be different depending on the height.

Third Embodiment

Figure 4A:
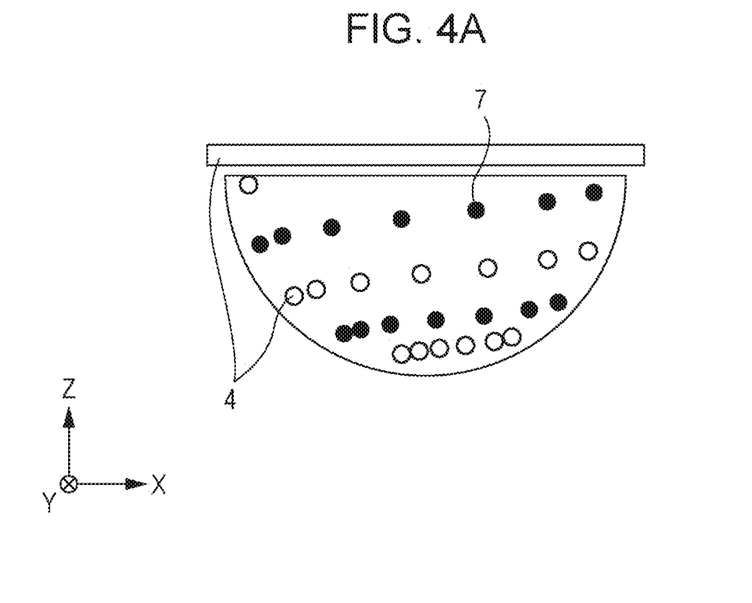
FIG. 4A is a schematic diagram for explaining a transducer and a light irradiation position according to a fourth embodiment of the present invention.
Figure 4B:
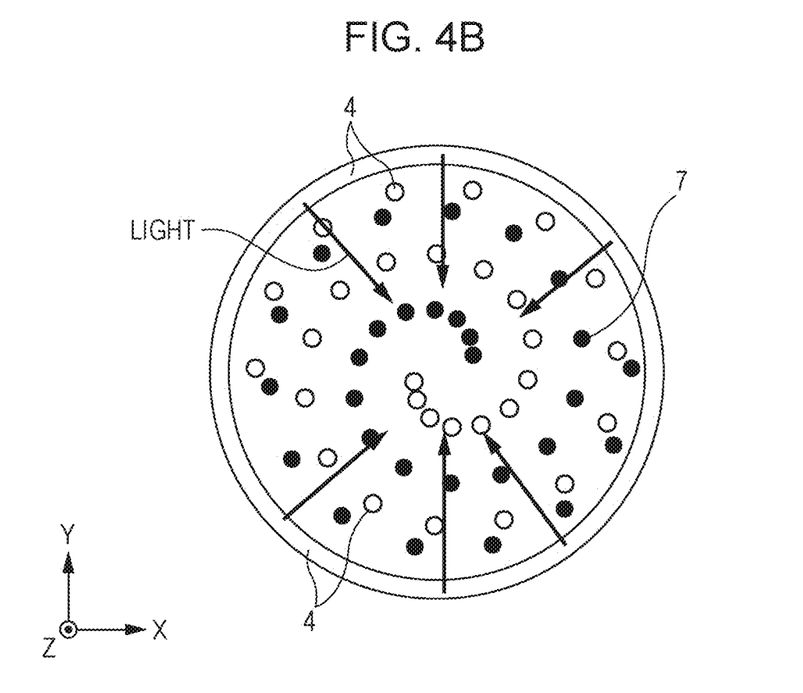
FIG. 4B is a schematic diagram for explaining the transducer and the light irradiation position according to the fourth embodiment of the present invention.

The present embodiment is characterized in that the light irradiation portions 4 are arranged near the opening of the detector. FIGS. 4A and 4B show the positions of the transducers 7 and the positions of the light irradiation portions 4 in the present embodiment. In FIG. 4, a light irradiation portion 4, which is not arranged on the detector 5 and which is arranged outside the surface of the detector and is not moved along with the rotation of the detector 5, is provided. The detector 5 has a hemispherical shape, and the subject 6 (for example, a breast) is inserted into the detector 5 from the opening. That is, the chest wall of the subject 6 is located higher than the height of the opening. It is desired that a part of the light irradiation positions are located outside and near the opening of the hemisphere in order to reduce attenuation of the light and irradiate the entire subject 6 with the light.

In the present embodiment, the light irradiation portions 4 are arranged on the detector 5, and at the same time, the light irradiation portion 4 is also arranged above the opening of the detector 5. In FIG. 4, the positions of the light irradiation portions 4 provided on the detector 5 are the same as those in the first embodiment. Although, in FIG. 4, the light irradiation portion 4 near the opening is separated from the detector and provided above the opening, the light irradiation portion 4 may be provided on the detector 5. However, when the opening of the detector 5 is located near the chest wall to irradiate the chest wall, the detector 5 may come into contact with the chest wall. Therefore, it is desired that the light irradiation portion 4 near the opening is provided above the opening separately from the detector 5 and the light irradiation portion 4 has a structure that does not rotate along with the detector 5. "Near the opening" means a position in a range of plus or minus 5 cm from the opening position or the opening in the rotation axis direction. Further, it is desired that a plurality of light irradiation portions 4 for irradiating the chest wall are arranged to surround the subject around the rotation axis.

Figure 9D:
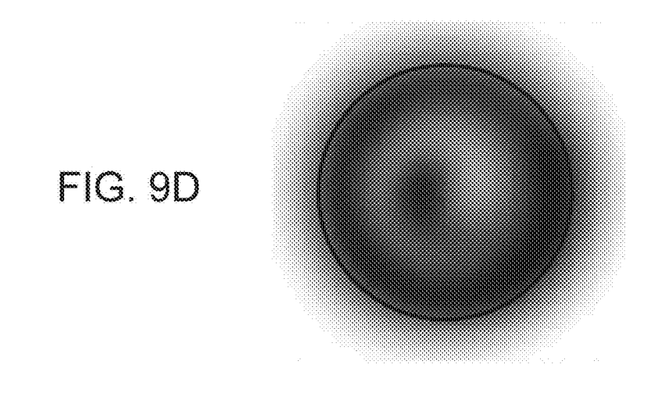
FIG. 9D is a schematic diagram showing the light intensity distribution formed by the third embodiment of the present invention.

FIG. 9D shows the light intensity distribution obtained by the present embodiment. Differently from the first embodiment (FIG. 9B), in the present embodiment, it is possible to irradiate the chest wall portion of the subject 6 (the opening portion of the detector) with light.

Fourth Embodiment

In the present embodiment, a configuration of the light irradiation portions 4 and the waveguide unit 3 is different from that of the first to the third embodiments. In the first to the third embodiments, optical fibers are used as the waveguide unit 3 and the measurement is performed by rotating the detector 5. At this time, end portions of the optical fibers, which are the light irradiation portions 4, move because the end portions are fixed to the detector 5. The other end portions (light incident portion 2) are in contact with the light source 1 and fixed. Therefore, the shape of the optical fibers is changed by the rotation. The larger the rotation angle is, the larger the load on the optical fiber is.

In the present embodiment, a configuration in which a waveguide unit 3 different from the optical fibers is used and the load on the waveguide unit 3 is small will be described. In the present embodiment, a space through which light is transmitted is formed between the detector 5 and the light source 1. The present embodiment is the same as the first embodiment except for the configuration of the light irradiation portions 4 and the waveguide unit 3, so that the differences from the first embodiment will be mainly described below.

Figure 5:
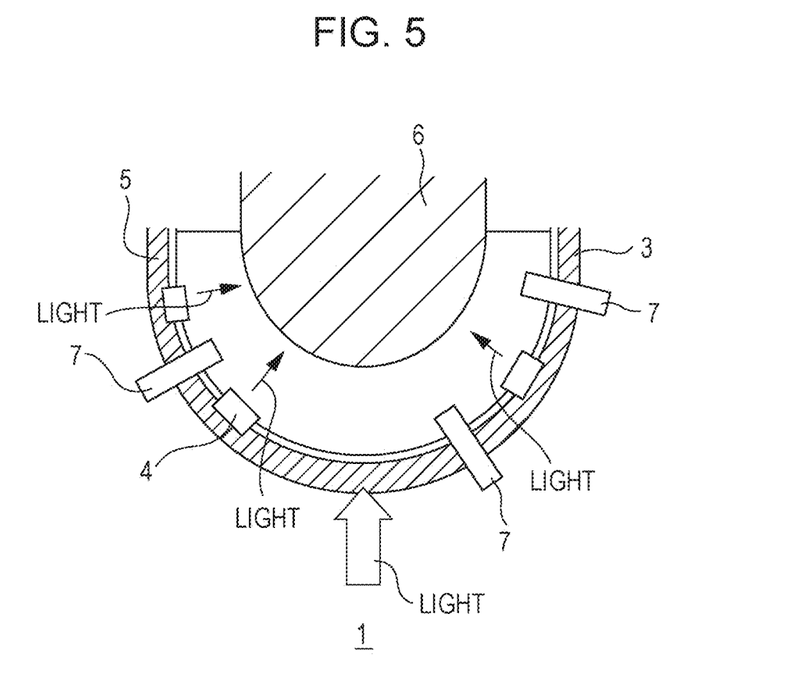
FIG. 5 is a schematic diagram for explaining an acoustic wave acquisition apparatus according to a fifth embodiment of the present invention.

As shown in FIG. 5, the waveguide unit 3 of the present embodiment has a structure surrounded by an inner surface of a hemisphere. The hemisphere surface included in the waveguide unit 3 is formed of a diffuse material. The light irradiated from the light source 1 is diffused by the diffuse material of the inner wall and spread inside the waveguide unit 3. The light irradiation portions 4 are portions which are included in the waveguide unit 3 and at which the diffuse material is not included, so that the light leaks from the waveguide unit 3. Or the light irradiation portions 4 may be formed of a diffuse material through which the light passes.

The width (width in the radial direction) of the waveguide unit 3 needs to be adjusted according to the curvature of the hemisphere surface so that the light is sufficiently diffused inside the waveguide unit 3. Further, a plurality of transducers 7 (including wiring portion) having an array shape cross the waveguide unit 3, so that it is desired that outer walls of the transducers 7 inside the waveguide unit 3 are covered with the diffuse material. A mirror surface (reflective surface) may be used as a substitute of the diffuse material.

The light is irradiated into the waveguide unit 3 by transmitting the light through a space using an optical system such as a lens, a mirror, or a prism. In the present embodiment, the light is irradiated from the rotation axis direction to the waveguide unit 3. Therefore, in the present embodiment, even when the detector 5 rotates, the shape of the waveguide unit 3 does not change. Therefore, it is possible to form a configuration in which the load on the waveguide unit 3 due to the rotational movement is small.

Fifth Embodiment

In a fourth embodiment, the configuration of the waveguide unit 3 is changed to reduce the load on the waveguide unit 3 including optical fibers caused by the rotational movement of the detector 5 and the end portions of the waveguide unit 3 (the light irradiation portions 4). In the present embodiment, a configuration will be described in which the waveguide unit 3 includes optical fibers and the arrangement of the transducers 7 is changed to reduce the rotation angle of the detector 5 in order to reduce the load on the optical fibers.

The rotation angle of the detector 5 is determined by the arrangement of the transducers 7. In the photoacoustic imaging, it is desired that the acoustic waves are received from a plurality of directions, so that the detector 5 rotates 360 degrees around the rotation axis in the first to the fourth embodiments. This is because only one of transducers 7 arranged on the detector 5 of the first to the fourth embodiments is disposed at each position (each height) in the rotation axis direction and when the detector rotates 360 degrees, the acoustic wave that reaches the height can be received from every direction.

Figure 6A:
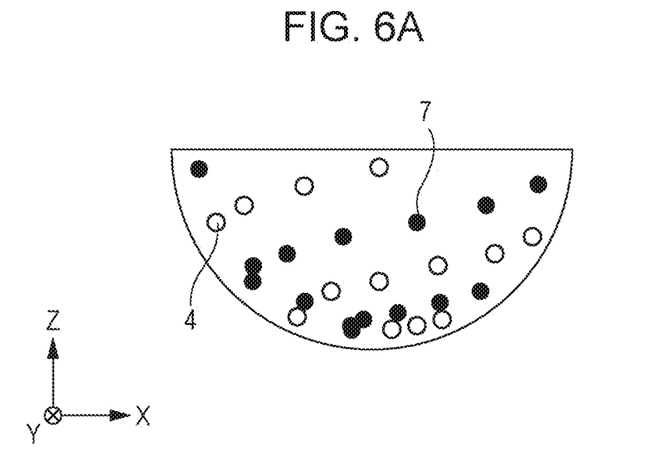
FIG. 6A is a schematic diagram for explaining a transducer and a light irradiation position according to a sixth embodiment of the present invention.
Figure 6B:
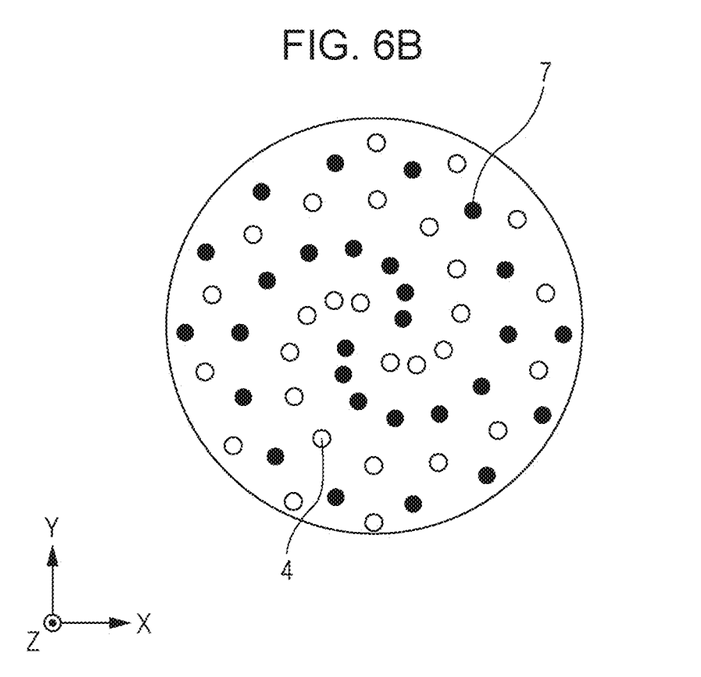
FIG. 6B is a schematic diagram for explaining the transducer and the light irradiation position according to the sixth embodiment of the present invention.

In the present embodiment, as shown in FIG. 6, two transducers 7 are disposed at predetermined positions in the rotation axis direction and the two transducers 7 are arranged to face each other so that the angle between the two transducers 7 with respect to the rotation axis is 180 degrees. This arrangement allows to reduce the rotation angle of the detector 5 to 180 degrees, which is one half of that in the first to the fourth embodiment. In FIG. 6, the number of the transducers 7 is 28, and 14 transducers form one helix. The light irradiation portions 4 has an arrangement obtained by rotating the arrangement of the transducers 7 by 90 degrees, and the light is irradiated from 28 positions.

In the measurement, the detector 5 is rotated 180 degrees by 8 steps. The rotation angle of the detector 5 is reduced by the structure of the present embodiment, so that the load on the optical fibers is reduced. In the present embodiment, not only the rotation angle but also the measurement time is reduced to one half.

Although, in the present embodiment, two transducers 7 are arranged at a specific height, the rotation angle can be further reduced by arranging more transducers 7 at a specific height. For example, when there are three transducers 7 at a specific height, the rotation angle is 120 degrees. The specific height of the transducers 7 may have a certain range, and it is possible to reduce the rotation angle by arranging transducers 7 located at a similar height to face each other.

Sixth Embodiment

The present embodiment is characterized in that the waveguide unit 3 rotates along with the detector 5 and a space is provided between the waveguide unit 3 and the light incident portion 2 in order to reduce the load on the waveguide unit 3 including optical fibers due to the rotation of the detector 5.

Figure 7A:
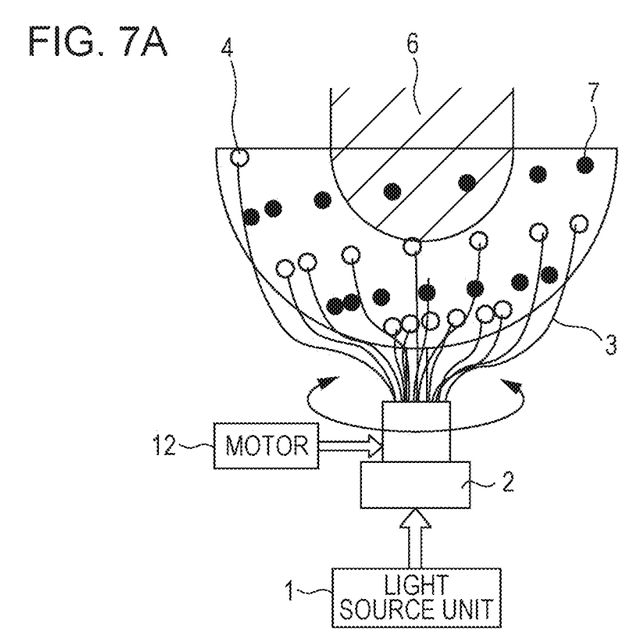
FIG. 7A is a schematic diagram for explaining an acoustic wave acquisition apparatus according to a seventh embodiment of the present invention.
Figure 7B:
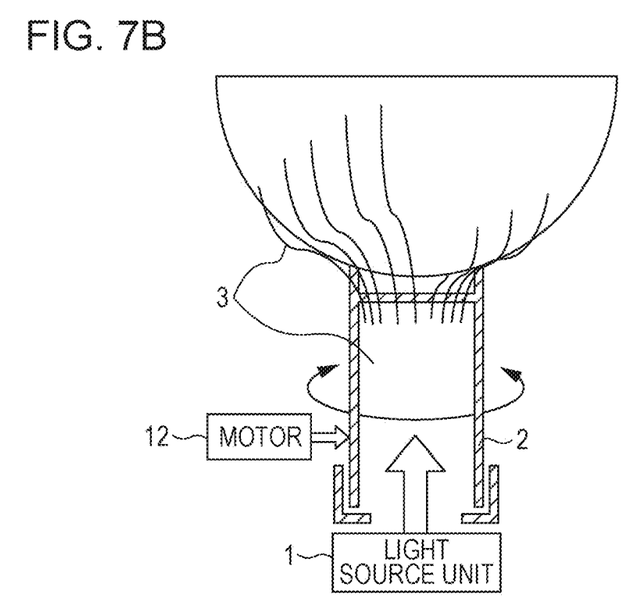
FIG. 7B is a schematic diagram for explaining the acoustic wave acquisition apparatus according to the seventh embodiment of the present invention.

FIG. 7A shows a configuration of the light source 1, the light incident portion 2, the waveguide unit 3, the detector 5, and the light irradiation portions 5. The end portions of the optical fibers of the waveguide unit 3 from which the light enters is integrated into one end portion and connected to the light incident portion 2 which is connected to the rotation motor and rotated along with the detector 5. A section of the light incident portion 2 to which the light is applied is not connected to the motor, so that the section does not rotate along with the detector 5. Therefore, as shown in FIG. 7B, the section of the light incident portion 2 to which the light is applied is not rotated and a section of the light incident portion 2 to which the waveguide unit 3 is connected is rotated. The light incident portion 2 is rotated along with the detector 5, so that it is possible to form a configuration in which the load on the waveguide unit 3 due to the rotational movement is small.

Seventh Embodiment

The present embodiment has a structure in which the light incident portion 2 moves along with the rotation of the detector 5 in order to reduce the load on the waveguide unit 3 including optical fibers due to the rotation of the detector 2.

Figure 8A:
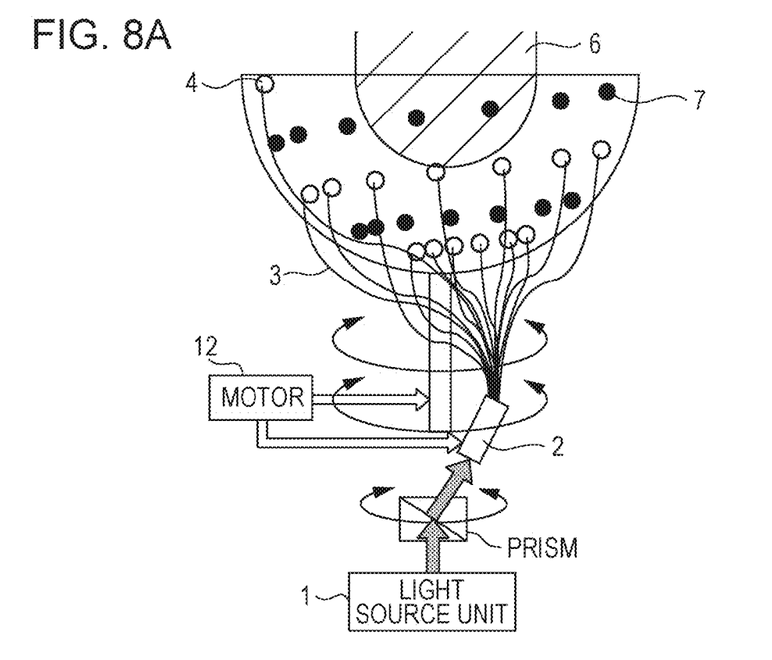
FIG. 8A is a schematic diagram for explaining an acoustic wave acquisition apparatus according to an eighth embodiment of the present invention.
Figure 8B:
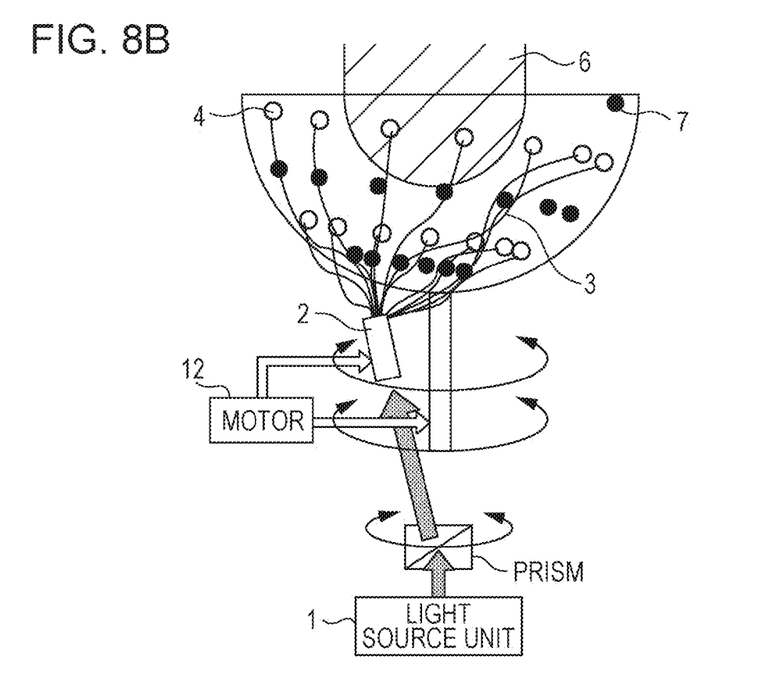
FIG. 8B is a schematic diagram for explaining the acoustic wave acquisition apparatus according to the eighth embodiment of the present invention.

FIGS. 8A and 8b show the present embodiment. When the measurement is performed, the waveguide unit 3 in which the optical fibers are bundled together is rotationally moved along with the rotation axis by the motor. The light incident position is also rotationally moved along with the rotation. Specifically, if the positional relationship between the light irradiation portions 4 and the light incident portion 2 is as shown in FIG. 9A, when the light irradiation portions 4 and the light incident portion 2 are rotated 180 degrees, the light incident position is also rotated 180 degrees as shown in FIG. 9B. The light from the light source, which is reflected and refracted by a prism, enters the light incident portion 2. To cause the light from the light source to enter the light incident portion 2 that is rotationally moved along with the detector 5, the optical path from the light source needs to be changed according to the movement of the light incident portion 2. Therefore, an angle of the prism that reflects the light from the light source is rotated along with the detector 5. The rotation of the prism is controlled in conjunction with the control unit 8 that controls and moves the motor.

Although, in the present embodiment, the light incident portion 2 is rotationally moved along with the detector 5, the light incident portion 2 may be moved to the extent that load is not applied to the optical fibers. For example, the light incident portion 2 may be rotated 180 degrees along with the rotation of the detector 5 or may be moved lineally. There may be a plurality of light incident portions 2 at a plurality of positions. The prism that changes the optical path may be replaced by a mirror, or the prism may not only change the optical path by the rotation, but also move to change the refraction angle and the reflection angle.

As described above, the present embodiment has a structure in which the light incident position rotates by the same angle as the rotation angle of the detector 5. Thereby, it is possible to form a configuration in which the shape of the waveguide unit 3 hardly changes even when the detector 5 rotates and the load on the waveguide unit 3 due to the rotational move is small.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-027320, filed Feb. 10, 2011, which is hereby incorporated by reference herein in its entirety.

REFERENCE SIGNS LIST

1 Light source
2 Light incidence portion
3 Waveguide unit
4 Light irradiation portion
5 Detector
6 Subject
7 Transducer

The invention claimed is:

1. An acoustic wave acquisition apparatus comprising:
a light source configured to generate light;
a detector including a plurality of elements configured to receive an acoustic wave generated from inside a subject when the subject is irradiated with the light;
a rotation driving unit configured to rotate the detector; and
a plurality of light irradiation portions configured to irradiate the subject with the light from the light source,
wherein the plurality of light irradiation portions are provided at least at positions other than a rotation axis of the detector,
wherein, when the plurality of light irradiation portions is seen from a rotation axis direction, a density of the plurality of light irradiation portions provided at a center area of the detector is different from a density of the plurality of light irradiation portions provided at a peripheral area of the detector.

2. The acoustic wave acquisition apparatus according to claim 1, wherein
the detector has a container shape into which the subject is inserted, and
the plurality of light irradiation portions are helically arranged on the detector.

3. The acoustic wave acquisition apparatus according to claim 1, wherein
the detector has a container shape into which the subject is inserted.

4. The acoustic wave acquisition apparatus according to claim 1, wherein
the detector has a container shape into which the subject is inserted, and
wherein the light irradiation portions are provided also near an opening of the detector having a container shape.

5. The acoustic wave acquisition apparatus according to claim 1, wherein
the light irradiation portions are provided also on the rotation axis.

6. The acoustic wave acquisition apparatus according to claim 1, further comprising:
a waveguide unit configured to guide the light generated by the light source to the light irradiation portions.

7. The acoustic wave acquisition apparatus according to claim 1, wherein, when the plurality of light irradiation portions is seen from the rotation axis direction, the density of the plurality of light irradiation portions provided at the center area of the detector is higher than the density of the plurality of light irradiation portions provided at the peripheral area of the detector.

8. The acoustic wave acquisition apparatus according to claim 1, wherein the plurality of light irradiation portions are provided at least at positions other than a rotation axis of the detector.

9. The acoustic wave acquisition apparatus according to claim 8,
wherein the detector has a container shape into which the subject is inserted, and
wherein the plurality of light irradiation portions are arranged rotationally symmetrically with respect to the rotation axis.

10. An acoustic wave acquisition apparatus comprising:
a light source configured to generate light;
a detector including a plurality of elements configured to receive an acoustic wave generated from inside a subject when the subject is irradiated with the light;
a rotation driving unit configured to rotate the detector; and
a plurality of light irradiation portions configured to irradiate the subject with the light from the light source,
wherein the plurality of light irradiation portions are provided at least at positions other than a rotation axis of the detector,
wherein the detector has a container shape into which the subject is inserted, and
wherein the plurality of light irradiation portions provided at least at the positions other than the rotation axis of the detector are arranged in a helical shape on the detector so that the plurality of light irradiation portions are provided at a plurality of positions in a rotation axis direction of the detector.

11. The acoustic wave acquisition apparatus according to claim 10,
wherein the plurality of elements are arranged in a helical shape on the detector, and
wherein the plurality of elements, and the plurality of light irradiation portions provided at least at the positions other than the rotation axis of the detector are arranged rotationally symmetrically with respect to the rotation axis.

12. The acoustic wave acquisition apparatus according to claim 10, wherein the plurality of light irradiation portions provided at least at the positions other than the rotation axis of the detector are arranged in such a manner that, when the plurality of light irradiation portions is seen from the rotation axis direction, an interval between two adjacent light irradiation portions becomes larger as irradiation portions are provided farther from the rotational axis of the detector.

13. An acoustic wave acquisition apparatus comprising:
a light source configured to generate light;
a detector including a plurality of elements configured to receive an acoustic wave generated from inside a subject when the subject is irradiated with the light;
a rotation driving unit configured to rotate the detector; and
a plurality of light irradiation portions configured to irradiate the subject with the light from the light source,
wherein the plurality of light irradiation portions are provided at least at positions other than a rotation axis of the detector,
wherein the detector has a container shape into which the subject is inserted, and
wherein the plurality of light irradiation portions provided at least at the positions other than the rotation axis of the detector are arranged rotationally symmetrically with respect to the rotation axis and are provided at a plurality of positions in a rotation axis direction of the detector.

14. The acoustic wave acquisition apparatus according to claim 13, wherein the rotation driving unit rotates the detector so that a light irradiation position does not change after rotation of the detector.

15. An acoustic wave acquisition apparatus comprising:
a light source configured to generate light;
a detector including a plurality of elements configured to receive an acoustic wave generated from inside a subject when the subject is irradiated with the light;
a rotation driving unit configured to rotate the detector;
a plurality of light irradiation portions configured to irradiate the subject with the light from the light source; and
a waveguide unit configured to guide the light generated by the light source to the light irradiation portions,
wherein the plurality of light irradiation portions are provided at least at positions other than a rotation axis of the detector,
wherein the acoustic wave acquisition apparatus is configured to reduce the load on the waveguide unit due to the rotation of the detector.

16. The acoustic wave acquisition apparatus according to claim 15, wherein,
the waveguide unit has a structure surrounded by the inner surface of the detector,
the surface included in the waveguide unit comprises a diffuse material so that the light irradiated from the light source is diffused by the diffuse material and spread inside the waveguide unit; and
the light irradiation portions are portions which are included in the waveguide unit and at which the diffuse material is not included, so that the light leaks from the waveguide unit.

17. The acoustic wave acquisition apparatus according to claim 15, wherein,
the waveguide unit has a structure surrounded by the inner surface of the detector,
the surface included in the waveguide unit comprises a diffuse material so that the light irradiated from the light source is diffused by the diffuse material and spread inside the waveguide unit; and
the light irradiation portion is formed of a diffuse material through with the light passes.

18. The acoustic wave acquisition apparatus according to claim 15, wherein,
the detector has a container shape into which the subject is inserted.

19. The acoustic wave acquisition apparatus according to claim 15, further comprising:
a light incident portion configured to guide the light generated by the light source to the waveguide unit, wherein
the waveguide unit rotates along with the detector,
a space is provided between the waveguide unit and the light incident portion.

20. The acoustic wave acquisition apparatus according to claim 15, further comprising:
a light incident portion configured to guide the light generated by the light source to the waveguide unit, wherein
the light incident portion moves along with the rotation of the detector and the light incident position rotates by the same angle as the rotation angle of the detector.

21. The acoustic wave acquisition apparatus according to claim 1, wherein the peripheral area of the detector is farther from the rotation axis than the center area of the detector.

22. The acoustic wave acquisition apparatus according to claim 1, wherein the center area of the detector crosses the rotation axis.

23. An acoustic wave acquisition apparatus comprising:
a light source configured to generate light;
a detector including a plurality of elements configured to receive an acoustic wave generated from inside a subject when the subject is irradiated with the light; and
a plurality of light irradiation portions configured to irradiate the subject with the light from the light source,
wherein a density of the plurality of light irradiation portions provided at a center area of the detector is different from a density of the plurality of light irradiation portions provided at a peripheral area of the detector.

24. The acoustic wave acquisition apparatus according to claim 23, wherein the detector has a container shape into which the subject is inserted.

25. The acoustic wave acquisition apparatus according to claim 24, wherein the light irradiation portions is provided also near an opening of the detector having a container shape.

26. The acoustic wave acquisition apparatus according to claim 23, wherein the density of the plurality of light irradiation portions provided at the center area of the detector is higher than the density of the plurality of light irradiation portions provided at the peripheral area of the detector.

27. The acoustic wave acquisition apparatus according to claim 23, further comprising:
a moving unit configured to move the detector.

* * * * *